United States Patent [19]
Cullinan et al.

[11] Patent Number: 5,643,896
[45] Date of Patent: Jul. 1, 1997

[54] 2-BENZYL-3-ARYLBENZOTHIOPHENES

[75] Inventors: George J. Cullinan, Trafalgar; James J. Sales, Indianapolis, both of Ind.

[73] Assignee: Eli Lilly and Company, Indianapolis, Ind.

[21] Appl. No.: 532,135

[22] Filed: Sep. 22, 1995

Related U.S. Application Data

[62] Division of Ser. No. 396,021, Feb. 28, 1995, Pat. No. 5,552,401.
[51] Int. Cl.$^6$ .................. A61K 31/38; A61K 31/445; C07D 333/64; C07D 409/10
[52] U.S. Cl. .................. 514/146; 514/324; 514/443; 514/442; 514/233.5; 549/51; 548/525; 540/596; 544/146; 546/202
[58] Field of Search .................. 514/324, 443, 514/442, 233.5, 146

[56] References Cited

U.S. PATENT DOCUMENTS

| | | | |
|---|---|---|---|
| 4,017,546 | 4/1977 | Suarez et al. | 568/327 |
| 4,075,223 | 2/1978 | Suarez et al. | 548/576 |
| 4,075,227 | 2/1978 | Jones et al. | 260/330.5 |
| 5,354,861 | 10/1994 | Sim et al. | 544/153 |

FOREIGN PATENT DOCUMENTS

| | | |
|---|---|---|
| 584952A1 | 3/1994 | European Pat. Off. |
| 617030A1 | 9/1994 | European Pat. Off. |
| 2647864 | 5/1977 | Germany. |

OTHER PUBLICATIONS

Jones et al., *J. Med. Chem*, 22, 962–966 (1979).
Jones et al., *J. Med. Chem.*, 27, 1057–1066 (1984).
Crenshaw et al., *J. Med. Chem.*, 14, (12), 1185–1190 (1971).
Draper, *J. Bone Miner. Met.*, 12, (2), 21–23 (1994).

Primary Examiner—Mukund J. Shah
Assistant Examiner—King Lit Wong
Attorney, Agent, or Firm—James J. Sales; David E. Boone

[57] ABSTRACT

The present invention provides a compound of formula I wherein $R_1$ is hydrogen, a hydroxy protecting group, or methyl;

$R_2$ and $R_3$ are independently $C_1$–$C_6$ alkyl, or $R_2$ and $R_3$, together with the nitrogen to which they are attached, form a heterocycle selected from the group consisting of pyrrolidino, hexamethyleneimino, morpholino, and piperidino;

Z is bromo, chloro, fluoro, hydroxy, a protected hydroxy, or hydrogen; and pharmaceutically acceptable salts and solvates thereof.

The present invention further provides pharmaceutical compositions containing compounds of formula I, optionally containing estrogen or progestin, and the use of such compounds alone, or in combination with estrogen or progestin, for alleviating the symptoms of post-menopausal syndrome, particularly osteoporosis, cardiovascular related pathological conditions, and estrogen-dependent cancer.

The compounds of the present invention also are useful for inhibiting uterine fibroid disease and endometriosis in women and aortal smooth muscle cell proliferation, particularly restenosis, in humans.

Also encompassed are novel intermediates.

8 Claims, No Drawings

2-BENZYL-3-ARYLBENZOTHIOPHENES

This application is a division, of application Ser. No. 08/396,021 filed Feb. 28, 1995, U.S. Pat. No. 5,552,401.

FIELD OF THE INVENTION

This invention relates to the fields of pharmaceutical and organic chemistry and provides novel benzothiophene compounds which are useful for the treatment of the various medical indications associated with post-menopausal syndrome, and uterine fibroid disease, endometriosis, and aortal smooth muscle cell proliferation.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of mensus. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new benzothiophene compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine fibroid disease, uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

Smooth aortal muscle cell proliferation plays an important role in diseases such as atherosclerosis and restenosis. Vascular restenosis after percutaneous transluminal coronary angioplasty (PTCA) has been shown to be a tissue response characterized by an early and late phase. The early phase occurring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology*, 8: 369–375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., *American Heart Journal*, 122: 171–187 (July 1991).

In the pathogenesis of restenosis excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use of compounds as smooth aortal muscle cell proliferation inhibitors and, thus inhibitors of restenosis.

SUMMARY OF THE INVENTION

The present invention relates to compounds of formula I

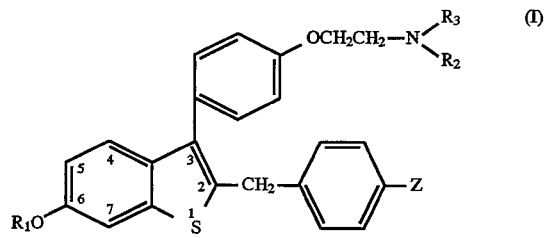

wherein

R₁ is hydrogen, a hydroxy protecting group, or methyl;

R₂ and R₃ are independently C₁–C₆ alkyl, or R₂ and R₃, together with the nitrogen to which they are attached, form a heterocycle selected from the group consisting of pyrrolidino, hexamethyleneimino, morpholino, and piperidino;

Z is bromo, chloro, fluoro, hydroxy, protected hydroxy, or hydrogen; and pharmaceutically acceptable salts and solvates thereof.

The present invention further relates to pharmaceutical compositions containing compounds of formula I, optionally containing estrogen or progestin, and the use of such compounds, alone, or in combination with estrogen or progestin, for alleviating the symptoms of post-menopausal syndrome, particularly osteoporosis, cardiovascular related pathological conditions, and estrogen-dependent cancer. As used herein, the term "estrogen" includes steroidal compounds having estrogenic activity such as, for example, 17β-estradiol, estrone, conjugated estrogen (Premarin®), equine estrogens, 17β-ethynyl estradiol, and the like. As used herein, the term "progestin" includes compounds having progestational activity such as, for example, progesterone, norethylnodrel, nongestrel, megestrol acetate, norethindrone, and the like.

The compounds of the present invention also are useful for inhibiting uterine fibroid disease and endometriosis in women and aortal smooth muscle cell proliferation, particularly restenosis, in humans.

Also provided are novel intermediates.

DETAILED DESCRIPTION OF THE INVENTION

One aspect of the present invention includes compounds of formula I

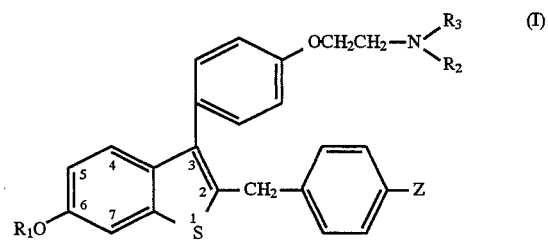

wherein $R_1$ is hydrogen, a hydroxy protecting group, or methyl;

$R_2$ and $R_3$ are independently $C_1-C_6$ alkyl, or $R_2$ and $R_3$, together with the nitrogen to which they are attached, form a heterocycle selected from the group consisting of pyrollidino, hexamethyleneimino, morpholino, and piperidino;

Z is bromo, chloro, fluoro, hydroxy, a protected hydroxy or hydrogen; and pharmaceutically acceptable salts and solvates thereof.

The invention also encompasses compounds of the formula (XIII)

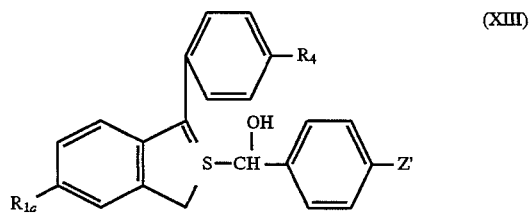

wherein $R_{1a}$ is hydroxy, protected hydroxy, or methoxy;

Z' is bromo, chloro, fluoro, hydrogen, hydroxy, or protected hydroxy; and $R_4$ is hydroxy, protected hydroxy, or a group of the formula

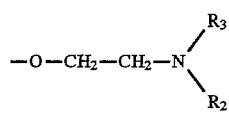

wherein $R_2$ and $R_3$ are independently $C_1-C_6$ alkyl, or together with the nitrogen to which they are attached, form a heterocycle selected from the group consisting of pyrollidino, hexamethyleneimino, morpholino, and piperidino; and salts and solvates thereof.

General terms used in the description of compounds herein described bear their usual meanings. For example, "$C_1-C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like.

The compounds of the invention may be prepared by methodology known in the art. For example, a 3-keto compound of the formula

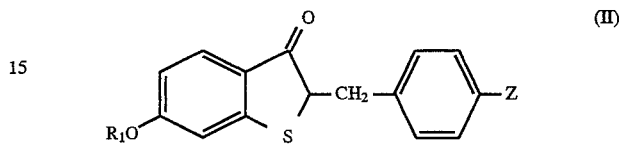

may be reacted with aryllithiumbromide (or aryl magnesium bromide) having the formula (III),

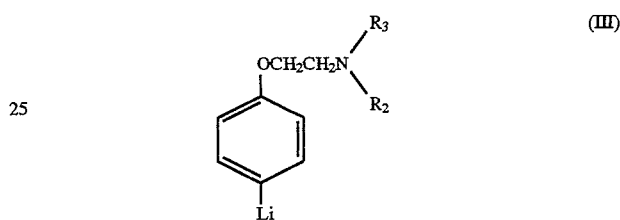

The reaction is desirably carried out in an unreactive solvent, such as tetrahydrofuran or ether. The reaction product is dehydrated by heating with hydrochloric acid in ethanol.

The product of the reaction may be isolated directly as the hydrochloride salt, or employing basification, as the free base. Further, the free base may employ a further salt formation to provide an acid-addition salt.

The compounds of formula (II) may be prepared by hydrogenation of the corresponding compounds of the formula (IV)

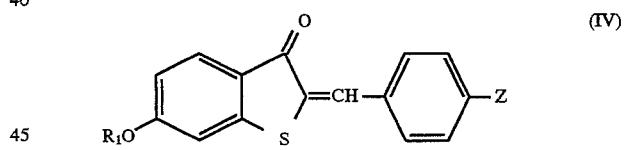

in the presence of a catalyst, such as palladium or platinum oxide, at room temperature. Suitable solvents for the reaction include alcohols and ethyl acetate.

Another example of synthesis involves reacting a compound of the formula (V)

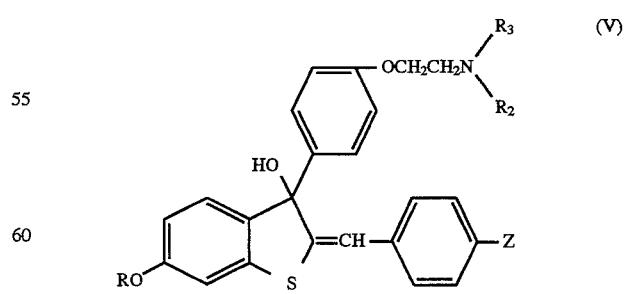

with magnesium bromide etherate, followed by treatment with lithium aluminum hydride. The compounds of formula (V) may be prepared by treating compounds of formula (IV) with aryllithium bromide (or aryl magnesium bromide) having the formula (III).

The compounds of formula (IV) may be synthesized in an analogous manner as set out in U.S. Pat. No. 5,354,861. A 3-keto-benzothiophene compound of formula (VI)

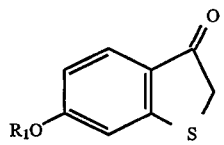

may be condensed with the appropriate aldehyde in catalytic amounts of hydrochloric acid.

Another method of preparation includes using an analogous method as described in Jones et al., U.S. Pat. No. 4,075,227, incorporated herein by reference. A thiol of the formula VII

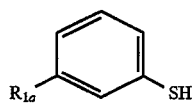

wherein $R_{1a}$ is a protected-hydroxy, is reacted with an α-haloacetophenone of the formula (VIII)

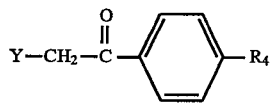

where $R_4$ is protected hydroxy, and Y is halo, to produce the compound of formula (IX)

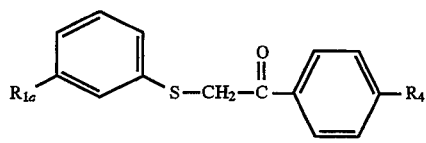

Compound IX is ring-closed in the presence of an acid, such as aryl sulfonic acid, an alkane sulfonic acid, sulfuric acid, polyphosphoric acid, or the like, to form a compound of formula (X)

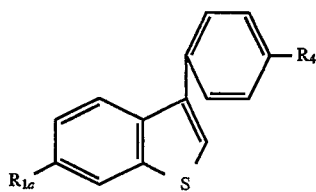

Compound X is then reacted in the presence of a Friedel-Crafts catalyst, such as aluminum chloride, with a benzoyl chloride of the formula (XI)

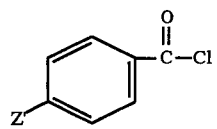

wherein

Z' is Z, or protected hydroxy, to produce

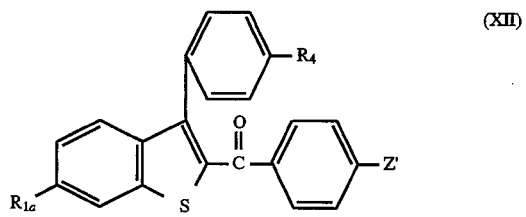

Compound XII is then placed in an appropriate solvent such as diethyl ether, THF, dioxane, or the like. Thereafter, Compound XII is reacted with a reducing agent, such as lithium aluminum hydride, (LAH), under an inert gas, such as nitrogen. The amount of reducing agent used is an amount sufficient to reduce the carbonyl to the carbinol of formula (XIII)

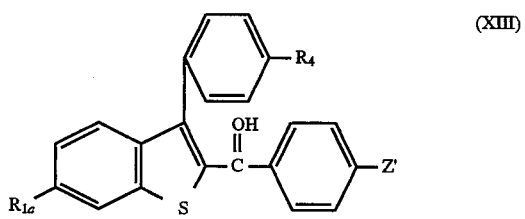

This intermediate is novel, as well as when $R_4$ is

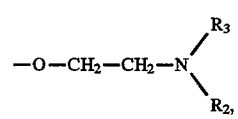

or when $R_{1a}$ is also hydroxy, or protected hydroxy, Z' is also hydroxy, and $R_4$ is also hydroxy. Thereafter, Compound XIII may be further reduced to provide the 2-methylene linker. This may be accomplished by placing Compound XIII in an appropriate solvent, and cooled under an inert gas. To this is added a suitable trialkylsilane reducing agent, preferably triethylsilyl, and a reasonably strong protic acid such as hydrochloric acid, trifluoracetic acid, or the like. Suitable solvents include dichloromethane, 1,2 dichloroethene, and chlorobenzene. The temperature for this reaction is between −5° C. to about 20° C. If $R_1$ and/or Z is hydroxy, $R_{1a}$ and Z' are protected hydroxys during the reaction, and the hydroxy protecting group (s) removed via known methodology.

To convert $R_4$ to

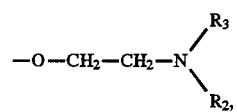

either prior to the reduction to the methylene or afterwards, any other hydroxy should be protected, and the compound (either XIII, or I, with any hydroxys protected) is treated with a moderately strong base, such as sodium hydroxide, in the presence of a compound of formula

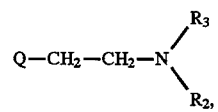

in which Q is halo, such as bromo or chloro.

Hydroxy protecting groups suitable for the above are known in the art. Preferred protecting groups include $C_1$-$C_4$ alkyl. See e.g., Barkin, "Protective Groups in Organic Chemistry," J. G. W. McOmie (ed.), Plenum Pass, NY, N.Y., 1973, Chapter 2, and Greene, "Protective Groups in Organic Synthesis," John Wiley and Sons, NY, N.Y., 1981, Chapter 7, in corporated herein by reference.

The following examples are intended to illustrate the invention described herein without unduly restricting it.

EXAMPLE 1

2-(p-Chlorobenzyl-3-[p-(2-dimethylaminoethoxy) phenyl]-6-methoxybenzo[b]thiophene)

n-Butyl lithium (5.27 ml, 7.80 mole) in THF is added dropwise to a solution of 4-[2-dimethylaminoethoxy]phenyl bromide (1.90 g, 7.80 mmol) in THF (5 ml) at −78° C. After stirring for 30 minutes at −78° C., 2-(p-chlorobenzyl)-6-methoxy-3-keto-(2H)benzothiophene (1.58 g, 5.20 mmol) in THF is added dropwise to the mixture at −78° C. The reaction mixture is stirred at −78° C. for 1 hour, and allowed to warm to room temperature. After stirring for 18 hours, it is quenched with saturated ammonium chloride and THF is evaporated off. The residue is dissolved in ethyl acetate (30 ml), washed with sodium chloride (2×20 ml), dried (anhydrous magnesium sulphate) and the solvent evaporated off. The remaining material is purified by flash chromatography (eluent, dichloromethane:hexane:triethylamine= 1:1:0.2). The alcohol without characterization is dehydrated. A solution of methanol (0.40 ml) saturated with dry hydrogen chloride gas is added to the tertiary alcohol dissolved in sodium-dried ether (40 ml). The product is formed and is filtered and recrystallized from ethanol to give the hydrochloride salt of the title compound.

EXAMPLE 2

2-(p-Chlorobenzyl)-3-[p-(2-(1-pyrollidino)ethoxy) phenyl]-6-methoxybenzo[b]thiophene 4-[2-(1-Pyrollidino)ethoxy]phenyl bromide (1.41 g, 5.20 mmol) in dry THF (50 ml) is added to magnesium turnings (312 mg, 13.0 mmol) in a dry 3-necked round bottom flask under an oxygen-free nitrogen atmosphere and the mixture is maintained under gentle reflux. 1,2-Dibromoethane (0.22 ml, 2.60 mmol) is added dropwise over a period of ½ hour. The mixture is heated gently until the magnesium is nearly consumed (ca. ½ hour). 2-(p-Chlorobenzyl)-6-methoxy-3-keto-(2H)benzothiophene (792 mg, 2.60 mmol) in THF (50 ml) is added dropwise to the mixture at 0° C. The reaction mixture is allowed to warm to room temperature and refluxed for 18 hours. The cooled mixture is quenched with saturated ammonium chloride (30 ml), extracted with dichloromethane (3×40 ml), washed with water, dried (anhydrous sodium sulphate) and the solvent evaporated off. The remaining material is dehydrated with concentrated hydrochloric acid (2 ml) in ethanol (25 ml). The mixture is refluxed for 2 hours, whereupon ethanol is removed. It is then basified with 10% sodium hydroxide (20 ml) and extracted with dichloromethane (3×40 ml). The dichloromethane extract is washed with water (3×20 ml), dried (anhydrous sodium sulphate) and the solvent is evaporated. Elution with (dichloromethane:hexane:triethylamine= 1:2:0.3), yields a crude titled product which is recrystallized from methanol to give titled product. Dry hydrogen chloride gas is bubbled through an ethereal solution of the free base for 10 minutes and cooled to 0° C. The hydrochloride salt which precipitated out is filtered off at the pump, rinsed with ether, and recrystallized from isopropanol to yield the hydrochloride salt.

EXAMPLE 3

2-(p-Chlorobenzyl)-3-[p-(2-(1-piperidino)ethoxy) phenyl]-6-methoxybenzo[b]thiophene n-Butyl lithium (5.27 ml, 7.80 mM) in THF is added dropwise to a solution of 4-[2-(1-piperidino)ethoxy]phenyl bromide (1.45 g, 7.80 mmol) in THF (5 ml) at −78° C. After stirring for 30 minutes at −78° C., 2-(p-chlorobenzyl)-6-methoxy-3-keto-(2H)benzothiophene (1.58 g, 5.20 mmol) in THF is added dropwise to the mixture at −78° C. The reaction mixture is stirred at −78° C. for 1 hour. It is warmed to room temperature. After stirring for 18 hours, it is quenched with saturated ammonium chloride and THF is evaporated off. The residue is dissolved in ethyl acetate (30 ml), washed with sodium chloride (2×20 ml), dried (anhydrous magnesium sulphate) and the solvent evaporated off. Thereafter, the material is purified by flash chromatography (eluent, dichloromethane:hexane:triethylamine= 1:1:0.2), and a solution of methanol (0.40 ml) saturated with dry hydrogen chloride gas is added to the material dissolved in sodium-dried ether (40 ml). The reaction mixture is stirred at room temperature for ½ hour. A precipitate is formed which is filtered and recrystallized from ethanol to give the hydrochloride salt of the title compound.

EXAMPLE 4

2-(p-Chlorobenzyl)-3-[p-(2-(1-morpholino)ethoxy) phenyl-6-methoxybenzo[b]thiophene (a) n-Butyl lithium (1.41 ml of a 1.56M solution, 2.2 mmol) is added dropwise to a solution of 4-[2-(1-morpholino)ethoxy]phenyl bromide (630 mg, 2.2 mmol) in THF (5 ml) at −78° C. After stirring for 30 minutes at −78° C., 2-(p-chlorobenzyl)-6-methoxy-3-keto-(2H) benzothiophene (609 mg, 2.0 mmol) in THF (2 ml) is added dropwise to the mixture at −78° C. The reaction mixture is allowed to warm to room temperature. After stirring for 18 hours, it is quenched with saturated ammonium chloride, THF is evaporated off to yield an alcohol which is dehydrated with concentrated hydrochloric acid (2 ml) in ethanol (10 ml). The mixture is refluxed for 2 hours, whereupon ethanol is removed. It is then basified with 10% sodium hydroxide (20 ml) and extracted with dichloromethane (3×40 ml).

The dichloromethane extract is washed with water (3×20 ml), dried (anhydrous sodium sulphate) and the solvent is evaporated off. The material is then eluted with dichromethane:hexane:triethylamine=1:2:0.3), and cooled to 0° C. Dry hydrogen chloride gas is bubbled for 10 minutes. The hydrochloride salt of the title compound is obtained after recrystallized from isopropanol.

(b) Magnesium bromide etherate (0.194 g, 0.75 mmol) is dissolved in 20 ml ether in a two-necked flask under oxygen-free nitrogen atmosphere at room temperature. After stirring for 1 hour, 2-(p-chlorophenylmethylene)-3-[p-(2-(1-morpholino)ethoxy)phenyl]-6-methoxy-2,3-dihydrobenzo [b]thiophen-3-ol (0.255 g, 0.5 mmol) in ether (10 ml) is added dropwise to the mixture. After stirring for 4 hours, LiAlH$_4$ (0.076 g, 2.0 mmol) is added to the above reaction mixture. The reaction mixture is left overnight at room temperature. After stirring overnight, ethyl acetate is added dropwise till hydrogen evolution ceased. The above mixture is washed with water followed by brine 2×20 ml), dried (anhydrous magnesium sulfate) and the solvent is evaporated off, followed by chromatography on silica. Elution with (chloroform:hexane:triethylamine=1:1:0.2) yields titled product.

EXAMPLE 5

2-(p-Chorophenylmethylene)-3-[p-(2-(1-morpholino)ethoxy)phenyl]-6-methoxy-2,3-dihydrobenzo[b]thiophen-3-ol n-Butyl lithium (2.87 mi of a 1.28M solution, 3.68 mmol) is added dropwise to solution of 4-[2-(1-morpholino)ethoxy] phenyl bromide (0.80 ml, 3.67 mmol) in THF (10 ml) at −78° C. under nitrogen atmosphere. After stirring for 1 hour at −78° C., 2-(p-chlorobenzylidene)-6-methoxy-3-ketobenzothiophene (1.06 g, 3.50 mmol) in THF is added dropwise to the mixture at −78° C. The reaction mixture is left overnight at room temperature. It is quenched with saturated ammonium chloride, THF is evaporated off, followed by extracting with ethyl acetate (2×20 ml). The ethyl acetate extract is washed with water followed by brine (2×20 ml), dried (anhydrous magnesium sulfate) and the solvent is evaporated, followed by chromatography on silica gel. Elution with (chloroform:hexane:triethylamine=1:1:0.2) yields titled product.

EXAMPLE 6

2-(p-Fluorobenzyl)-3-[p-(2-diethylaminoethoxy) phenyl]-6-methoxybenzo[b]thiophene The methods of Example 5 followed by Example 4b are used for the preparation of 2-(p-fluorobenzyl)-3-[p-(2-diethylaminoethoxy)phenyl]-6-methoxybenzo[b]thiophene. The specific gram proportions of reactants used are similar and are not meant to be limiting and can be varied around idealized stoichiometric proportion in the usual way known to those skilled in the art.

EXAMPLE 7

2-(p-Fluorobenzyl)-3-[p-(2-(1-pyrollidino)ethoxy) phenyl]-6-methoxybenzo[b]thiophene The methods of Example 5 followed by Example 4b are used for the preparation of 2-(p-fluorobenzyl)-3-[p-(2-(1-pyrollidino)ethoxy)phenyl]-6-methoxybenzo[b]thiophene.

EXAMPLE 8

2-(p-Fluorobenzyl)-3-[p-(2-(1-piperidino)ethoxy) phenyl]-6-methoxybenzo[b]thiophene The methods of Example 5 followed by Example 4b are used for the preparation of 2-(p-fluorobenzyl)-3-[p-(2-(1-piperidino)ethoxy)phenyl]-6-methoxybenzo[b]thiophene.

EXAMPLE 9

2-(p-Fluorobenzyl)-3-[p-(2-(1-morpholino)ethoxy) phenyl]-6-methoxybenzo[b]thiophene The methods of Example 5 followed by Example 4b are used for the preparation of 2-(p-fluorobenzyl)-3-[p-(2-(1-morpholino)ethoxy)phenyl]-6-methoxybenzo[b]thiophene.

EXAMPLE 10

2-(p-Methoxyphenyl)-3-[p-(2-(1-piperidenyl)ethoxy) phenyl]-6-methoxy benz[b]thiophene The methods of Example 5 followed by Example 4b are used for the preparation of 2-(p-Methoxyphenyl)-3-[p-(2-(1-piperidenyl)ethoxy) phenyl]-6-methoxy benz[b] thiophene.

Although the free-base form of formula I compounds can be used in the methods of the present invention, it may be preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

TEST PROCEDURE

General Preparation Procedure

In the examples illustrating the methods, a postmenopausal model is used in which effects of different treatments upon circulating lipids were determined.

Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and had ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection

After a one week acclimation period (therefore, two weeks post-OVX) daily dosing with test compound is initiated. 17°-ethynyl estradiol or the test compound are given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis

Blood samples are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

Uteri are kept at 4° C. until time of enzymatic analysis. The uteri are then homogenized in 50 volumes of 50 mM Tris buffer (pH—8.0 containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Source of Compound

17α-ethynyl estradiol is obtained from Sigma Chemical Co., St. Louis, Mo.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl β-cyclodextrin are orally administered to test animals.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium (Ca++/Mg++ free HBSS (phenol red-free) supplemented with 10 mM HEPES and 2 mM EDTA). Cells are washed twice with assay medium and adjusted to 80,000 cells/mL. Approximately 100 µL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 µL transferred to triplicate microcultures followed by 50 µL assay medium for a final volume of 200 µL. After an additional 48 hours at 37° C. in a 5% $CO_2$ humidified incubator, microcultures are pulsed with tritiated thymidine (1 uCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace β counter.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Assay 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Assay 2

The same procedure is used as in Test 1, except the period of administration is 6 months.

Assay 3

The same procedure is used as in Test 1, except the period of administration is 1 year.

Assay 4

A. Induction of Fibroid Tumors in Guinea Pig

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of Human Uterine Fibroid Tissue in Nude Mice

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Assay 5

A. Tissue from human uterine fibroid tumors is harvested and maintained, in vitro, as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Assay 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Assay 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Assay 3

A. Surgical Induction of Endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of Human Endometrial Tissue in Nude Mice

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Assay 4

A. Tissue from human endometrial lesions is harvested and maintained in vitro as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Aortal Smooth Cell Proliferation/Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res*, 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above assays indicates that the compounds of the present invention are of potential in the treatment of restenosis.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation. The following formulation examples only are illustrative and are not intended to limit the scope of the present invention.

Formulations

In the formulations which follow, "active ingredient" means a compound of formula I, or a salt or solvate thereof.

Formulation 1: Gelatin Capsules
Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
|---|---|
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3-: Tablets

| Ingredient | Quantity (mg/tablet) |
|---|---|
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 50 mg |
| Isotonic saline | 1,000 mL |

The solution of the above ingredients is intravenously administered to a patient at a rate of about 1 mL per minute.

Formulation 8: Combination Capsule I

| Ingredient | Quantity (mg/capsule) |
|---|---|
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
|---|---|
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
|---|---|
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:

1. A method for alleviating the symptoms of post-menopausal syndrome comprising administering to a woman in need of such treatment an effective amount of a compound of formula I

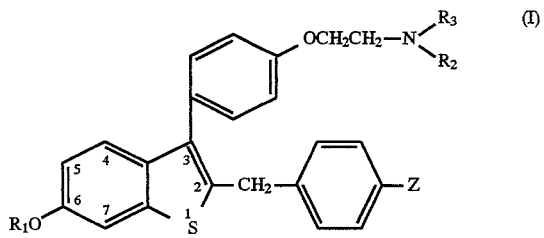

wherein $R_1$ is hydrogen, a hydroxy protecting group, or methyl;

$R_2$ and $R_3$ are independently $C_1-C_6$ alkyl, or $R_2$ and $R_3$, together with the nitrogen to which they are attached, form a heterocycle selected from the group consisting of pyrrolidino, hexamethyleneimino, morpholino, and piperidino;

Z is bromo, chloro, fluoro, hydroxy, protected hydroxy, or hydrogen; and pharmaceutically acceptable salts and solvates thereof.

2. A method according to claim 1 wherein the post-menopausal syndrome pathological condition is osteoporosis.

3. A method according to claim 1 wherein the post-menopausal syndrome pathological condition is related to a cardiovascular disease.

4. A method according to claim 3 wherein the cardiovascular disease is hyperlipidemia.

5. A method for inhibiting uterine fibroid disease comprising administering to a woman in need of such treatment an effective amount of a compound of formula I

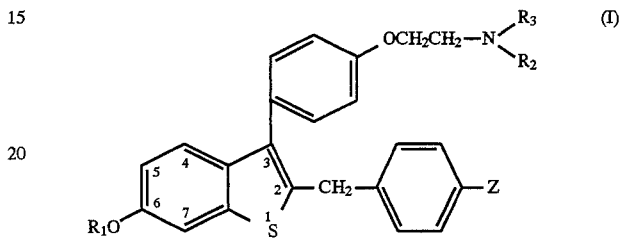

wherein $R_1$ is hydrogen, a hydroxy protecting group, or methyl;

$R_2$ and $R_3$ are independently $C_1-C_6$ alkyl, or $R_2$ and $R_3$, together with the nitrogen to which they are attached, form a heterocycle selected from the group consisting of pyrrolidino, hexamethyleneimino, morpholino, and piperidino;

Z is bromo, chloro, fluoro, hydroxy, protected hydroxy, or hydrogen; and pharmaceutically acceptable salts and solvates thereof.

6. A method for inhibiting endometriosis comprising administering to a woman in need of such treatment an effective amount of a compound of formula I

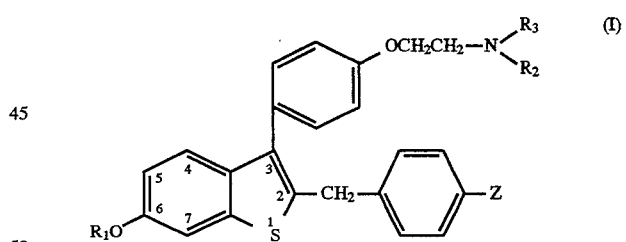

wherein $R_1$ is hydrogen, a hydroxy protecting group, or methyl;

$R_2$ and $R_3$ are independently $C_1-C_6$ alkyl, or $R_2$ and $R_3$, together with the nitrogen to which they are attached, form a heterocycle selected from the group consisting of pyrrolidino, hexamethyleneimino, morpholino, and piperidino;

Z is bromo, chloro, fluoro, hydroxy, protected hydroxy, or hydrogen; and pharmaceutically acceptable salts and solvates thereof.

7. A method for inhibiting aortal smooth muscle cell proliferation comprising administering to a human in need of such treatment an effective amount of a compound of formula I

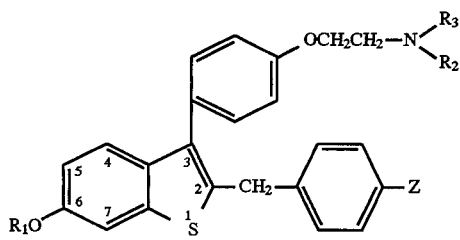 (I)

wherein

R₁ is hydrogen, a hydroxy protecting group, or methyl;

R₂ and R₃ are independently $C_1$–$C_6$ alkyl, or R₂ and R₃, together with the nitrogen to which they are attached, form a heterocycle selected from the group consisting of pyrrolidino, hexamethyleneimino, morpholino, and piperidino;

Z is bromo, chloro, fluoro, hydroxy, protected hydroxy, or hydrogen; and pharmaceutically acceptable salts and solvates thereof.

8. A method for inhibiting restenosis comprising administering to a human in need of such treatment an effective amount of a compound of formula I

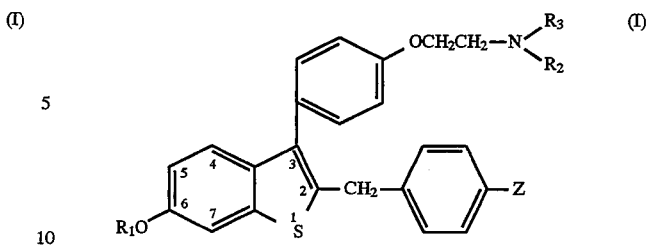 (I)

wherein

R₁ is hydrogen, a hydroxy protecting group, or methyl;

R₂ and R₃ are independently $C_1$–$C_6$ alkyl, or R₂ and R₃, together with the nitrogen to which they are attached, form a heterocycle selected from the group consisting of pyrrolidino, hexamethyleneimino, morpholino, and piperidino;

Z is bromo, chloro, fluoro, hydroxy, protected hydroxy, or hydrogen; and pharmaceutically acceptable salts and solvates thereof.

* * * * *